United States Patent
Cover et al.

(10) Patent No.: US 8,545,396 B2
(45) Date of Patent: Oct. 1, 2013

(54) WIRELESS ENDOSCOPIC CAMERA

(75) Inventors: Reid Cover, Mountain View, CA (US); Emmet McCarthy, Gilroy, CA (US); Vasudev Nambakam, San Jose, CA (US)

(73) Assignee: Stryker Corporation, Kalamazoo, MI (US)

(*) Notice: Subject to any disclaimer, the term of this patent is extended or adjusted under 35 U.S.C. 154(b) by 1711 days.

(21) Appl. No.: 11/985,572

(22) Filed: Nov. 15, 2007

(65) Prior Publication Data

US 2008/0139881 A1    Jun. 12, 2008

Related U.S. Application Data

(60) Provisional application No. 60/859,413, filed on Nov. 16, 2006.

(51) Int. Cl.
*A61B 1/04* (2006.01)
*A61B 1/06* (2006.01)
*A61B 1/00* (2006.01)

(52) U.S. Cl.
USPC .................. 600/109; 600/160; 600/101

(58) Field of Classification Search
USPC .................. 600/109, 160, 112, 172–175
See application file for complete search history.

(56) References Cited

U.S. PATENT DOCUMENTS

| 5,166,787 A | 11/1992 | Irion |
| 5,264,925 A | 11/1993 | Shipp et al. |
| 5,929,901 A | 7/1999 | Adair et al. |
| 6,043,839 A | 3/2000 | Adair et al. |
| 6,106,457 A | 8/2000 | Perkins et al. |
| 6,141,037 A | 10/2000 | Upton et al. |
| 6,428,470 B1* | 8/2002 | Thompson ............ 600/173 |
| 6,449,006 B1 | 9/2002 | Shipp |
| 6,612,981 B2 | 9/2003 | Onishi et al. |
| 6,692,431 B2 | 2/2004 | Kazakevich |
| 6,730,019 B2 | 5/2004 | Irion |

(Continued)

FOREIGN PATENT DOCUMENTS

| DE | 100 28 081 A1 | 2/2001 |
| EP | 1 215 893 A1 | 6/2002 |

(Continued)

OTHER PUBLICATIONS

English translation of First Office Action from corresponding China Appl. 200780042577.7 dated Sep. 13, 2010 (6 pages).

(Continued)

*Primary Examiner* — Philip R Smith
*Assistant Examiner* — William Chou
(74) *Attorney, Agent, or Firm* — Flynn, Thiel, Boutell & Tanis, P.C.

(57) ABSTRACT

A system and method for wirelessly transmitting a video image signal from an endoscopic camera to a receiver or control unit for storage and/or display on a video monitor. Use of a frame-specific, variable compression algorithm capable of progressively encoding a data stream provides for a better performing and higher quality wireless endoscopic camera system capable of generating images at varying resolutions. Use of a short-range, high-performance wireless technology, such as Ultrawideband (UWB), improves the performance capabilities of the system, while minimizing power consumption and extending battery life. Implementations of error correcting codes, as well as the use of multiple transmitting and receiving antennas, further improve the fidelity of the wireless communication.

19 Claims, 13 Drawing Sheets

(56) References Cited

U.S. PATENT DOCUMENTS

| | | | |
|---|---|---|---|
| 6,761,561 | B2 | 7/2004 | Mandelkern et al. |
| 6,770,027 | B2 | 8/2004 | Banik et al. |
| 6,782,285 | B2 | 8/2004 | Birkenbach et al. |
| 6,840,901 | B2 | 1/2005 | Onishi et al. |
| 6,902,529 | B2 | 6/2005 | Onishi et al. |
| 7,030,904 | B2 | 4/2006 | Adair et al. |
| 7,063,663 | B2 | 6/2006 | Kazakevich |
| 7,664,174 | B2 * | 2/2010 | Avni et al. ................ 375/240.01 |
| 8,246,230 | B2 * | 8/2012 | Todd et al. .................... 362/574 |
| 2002/0120181 | A1 | 8/2002 | Irion |
| 2002/0184122 | A1 | 12/2002 | Yamaguchi et al. |
| 2003/0137588 | A1 | 7/2003 | Wang et al. |
| 2004/0147809 | A1 | 7/2004 | Kazakevich |
| 2004/0196364 | A1 | 10/2004 | Takahashi |
| 2004/0249247 | A1 | 12/2004 | Iddan |
| 2005/0111746 | A1 | 5/2005 | Kumar et al. |
| 2005/0177024 | A1 | 8/2005 | Mackin |
| 2005/0190850 | A1 | 9/2005 | Takano |
| 2005/0197533 | A1 | 9/2005 | May et al. |
| 2005/0237971 | A1 | 10/2005 | Skraparlis |
| 2005/0272975 | A1 * | 12/2005 | McWeeney et al. .......... 600/113 |
| 2006/0034514 | A1 | 2/2006 | Horn |
| 2006/0219776 | A1 * | 10/2006 | Finn .............................. 235/380 |
| 2007/0060789 | A1 * | 3/2007 | Uchimura et al. ............ 600/110 |
| 2008/0021273 | A1 * | 1/2008 | MacKin ........................ 600/109 |
| 2010/0022833 | A1 * | 1/2010 | Nagase ......................... 600/118 |

FOREIGN PATENT DOCUMENTS

| | | |
|---|---|---|
| EP | 1 638 333 A1 | 3/2006 |
| GB | 2 196 211 A | 4/1988 |
| JP | 6-335450 | 12/1994 |
| JP | 9-182715 | 7/1997 |
| JP | 2001251612 | 9/2001 |
| JP | 2004305373 | 11/2004 |
| JP | 2006-239053 | 9/2006 |
| JP | 2007522686 | 8/2007 |
| WO | WO 93/15648 | 8/1993 |
| WO | WO 2006/077966 A1 | 7/2006 |

OTHER PUBLICATIONS

International Search Report and Written Opinion of the International Searching Authority, mailed Sep. 4, 2008 (23 sheets).

Trenschel T M, et al., Region-Based Guaranteed Image Quality in JPEG2000, ICICS-PCM 2003, Dec. 15-18, 2003 Singapore, pp. 464-468.

English translation of Japan Office Action dated Aug. 30, 2012 (4 pages).

* cited by examiner

WIRELESS ENDOSCOPIC CAMERA

CROSS REFERENCE TO RELATED APPLICATION

This application claims the benefit of U.S. Provisional Application No. 60/859,413, filed Nov. 16, 2006, the disclosure of which is incorporated herein by reference in its entirety.

FIELD OF THE INVENTION

The present invention relates to a reliable, high-performance wireless endoscopic camera system and corresponding method for wirelessly transmitting images from an endoscopic camera head to a control unit.

BACKGROUND OF THE INVENTION

Endoscopy is a technology that allows minimally-invasive viewing of internal features of the body of a patient. In medicine, endoscopy allows acquisition of high-quality images of internal features of a human body without the need for invasive surgery. The basic tool of endoscopy is the endoscope, which is inserted into the patient's body to be viewed. Some endoscopic procedures involve the use of a flexible scope, as in the medical field of gastroenterology, for example. Other medical procedures, such as arthroscopy or laproscopy, use a rigid scope. The scope is normally coupled to a high-intensity light source that transmits light into the body through the scope. Reflected light representing images of the body interior then enters the scope and is directed to a camera head that includes electronics for acquiring video image data. The camera head is typically coupled directly to a video monitor or other display device, or alternatively to an intermediate video processing system, for displaying and/or recording the video images acquired by the camera.

In traditional endoscopes, a wired connection (i.e., cable) is used to physically connect the camera head to a video monitor or processing system. Images viewed by the endoscope are converted to video image data by the camera head and then transmitted over the wired connection to the video monitor for display.

Unfortunately, the presence of the wired connection between the camera head and monitor lead to various complications. First, the presence of a wired connection on the camera head makes it difficult for the surgeon to operate since the wired connection often interferes with free movement of the endoscope. In addition, a camera head utilizing a wired connection poses a greater risk of contamination during surgery. The endoscope and associated camera head are surgical tools, and as such, are utilized within the "sterile field", a defined area around the patient where only sterilized objects are allowed. However, the devices that connect to the camera head, i.e., video monitor, video recorder, etc., cannot be sterilized, and thus must be maintained outside the sterile field. The wired connection subsequently complicates the maintaining of a sterile field since a physical link exists between the sterile camera head and the non-sterile monitor.

To address the above problems, manufacturers have begun producing endoscopic camera heads that incorporate a transmitter for wirelessly conveying the video image data to the devices outside the sterile field. This, however, leads to various new problems. Wireless communications are frequently subject to various types of electromagnetic interference, resulting in the camera heads being unreliable. Disruption of the wireless signal due to obstruction can also be a problem. During a procedure, a surgeon may frequently change their hold on the camera head or endoscope, resulting in the antenna of the camera head to be covered over or blocked. Surgeons can also be quite mobile during a procedure, changing their position relative to the patient's body in order to improve their view or obtain better access. Consequently, the position of the camera head can change frequently, thereby increasing the chance that the wireless signal path may become obstructed by an object in the room or even by the surgeon's body. Additionally, the wireless connection between the camera head and monitor can be limited to a relatively low rate of data transfer, thereby restricting the transfer of the more bandwidth intensive high-fidelity digital video signal. Limitations in the image compression schemes typically utilized by existing endoscopic cameras also tend to decrease the reliability of the wireless connection as well as impose limitations on the quality of the video.

SUMMARY OF THE INVENTION

A wireless endoscopic camera system capable of providing a reliable but high-performance wireless transmission of video image data from an endoscope camera head to a control unit. A high sensitivity image sensor allows for image capturing in low light conditions. The video image data then undergoes a lossy or lossless variable compression process according to one embodiment. Increased fidelity of the signal is achieved in another embodiment through implementation of one or more error correcting codes.

In an additional embodiment, a high-performance, short-range wireless technology, such as UWB, is utilized to convey the video image signal from the camera head to the control unit.

Increased battery life of the camera head is also achieved due to the reduced power requirements of the wireless technology.

To minimize miscommunication or interference between multiple systems, each system of a further embodiment can be provided the ability to lock or synchronize one transmitter to one receiver, thereby assuring that the control unit will only acknowledge wireless signals from its corresponding camera head.

A portable power source, such as a rechargeable battery, provides power to the camera head. According to one embodiment, the camera head can simultaneously accommodate at least portable power sources, thereby allowing one source to be replaced while the other source continues to power the camera head. In the event of an emergency, such as a lack of charged batteries or a disruption in wireless communication, another embodiment incorporates the use of a sterilizable backup cable that can connect the camera head to the control unit and allow the camera head to continue operating.

To improve the fidelity of the wireless link between camera head and control unit, a further embodiment incorporates the use of multiple antennas for either one or both of the camera head and control unit. The multiple antennas can be configured into numerous arrangements and positions on the camera head as well as within the operating room.

BRIEF DESCRIPTION OF THE DRAWINGS

One or more embodiments of the present invention are illustrated by way of example and should not be construed as being limited to the specific embodiments depicted in the accompanying drawings, in which like references indicate similar elements and in which.

DETAILED DESCRIPTION

Figure 1:
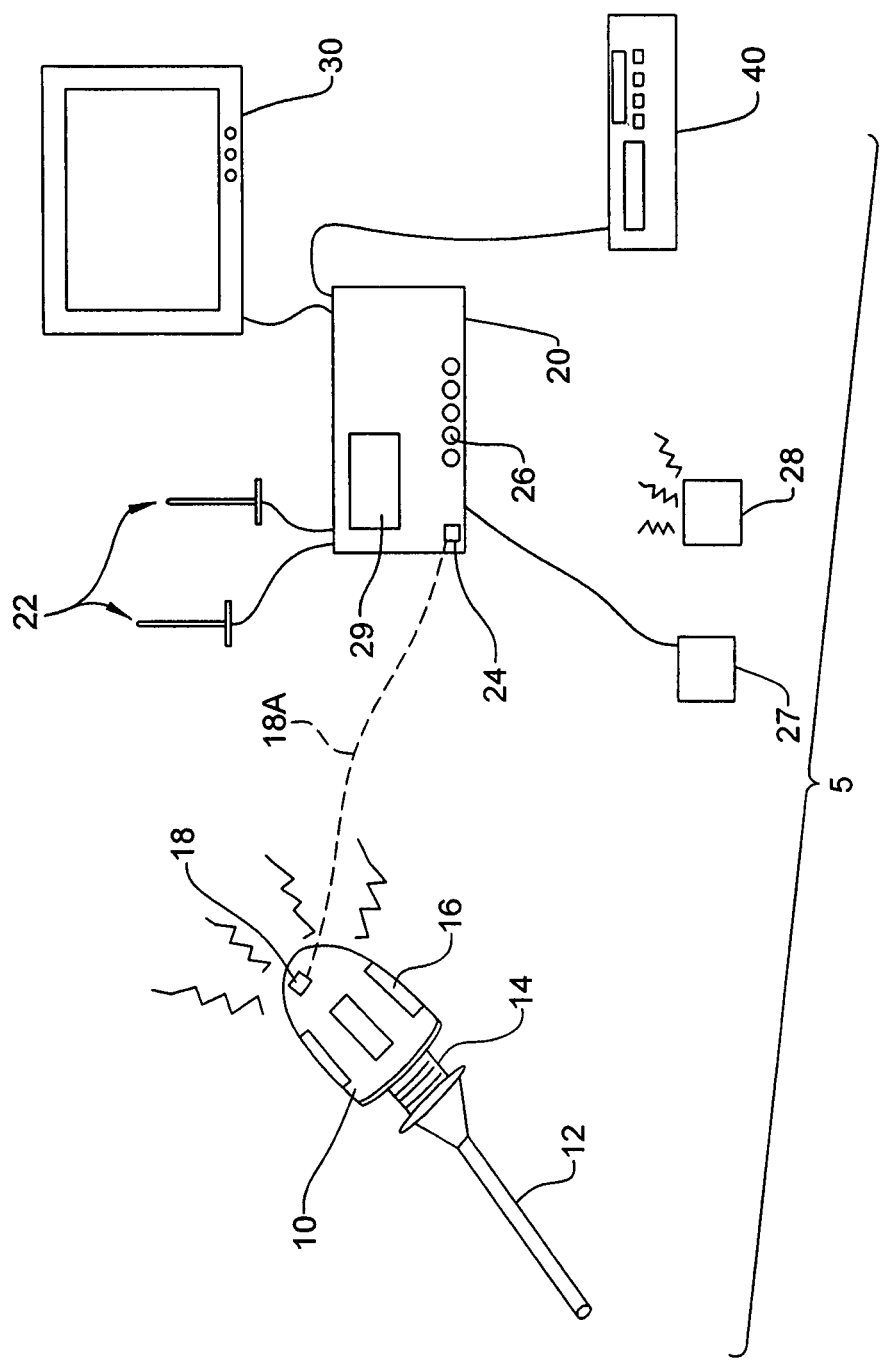
FIG. 1 illustrates a wireless endoscopic camera system according to one embodiment of the invention.

FIG. 1 depicts a wireless endoscopic camera system 5 according to one embodiment of the present invention. A wireless camera head 10 detachably mounts to an endoscope 12 by a connector 14. Contained within camera head 10 is a battery powering the electronics for the camera itself as well as the electronics making up the wireless transmitter system. Incorporated within or mounted upon the camera head 10 are one or more antennas 16 for directing the wireless signal to a receiver. The camera head 10 can also include one or more interfaces 18, such as a jack, for receiving a wired connection capable of providing power to the camera head 10 and/or for the transfer of video image data.

Located outside the sterile field is a control unit 20 that subsequently receives and processes the wireless video signal transmitted by the camera head 10. Associated with the control unit 20 are one or more antennas 22 for intercepting and conveying the wireless video signal to the control unit 20. These antennas 22 may be incorporated within, attached to, or placed adjacent or remotely to the control unit 20. Alternatively, an interface 24 may be provided on the central control unit 20 for receiving a wired connection for the transfer of data, as well as various controls or switches 26 and incorporated display 29. A video monitor 30 connects to the control unit 20 for receiving and displaying the video signal from camera head 10. According to an additional embodiment, control unit 20 can also connect to, or communicate with, one or more wired or wireless remote controls, 27 and 28, respectively. Additional video processing equipment 40, such as, for example, a video recorder or printer, may also be placed in communication with the control unit 20.

The camera system 5 includes at least one transmitting antenna 16 associated with the camera head 10. Similarly, the system includes at least one receiving antenna 22 associated with the control unit 20. Alternatively, the system can utilize multiple transmitting antennas and/or receiving antennas in various configurations in order to improve the fidelity and reliability of the wireless signal.

For example, according to one embodiment, the wireless endoscopic camera system 5 is configured to operate in a multiple input, single output (MISO) mode by having a camera head 10 provided with a single transmitting antenna 16, while the control unit 20 is provided with multiple receiving antennas 22 that can be placed at various locations throughout the operating room. Alternatively, the system 5 may be configured to operate in a single input, multiple output (SIMO) mode by having a camera head 10 provided with multiple transmitting antennas 16, while the control unit 20 is provided with a single receiving antenna 22. According to yet another embodiment, the camera system 5 is provided with greater wireless gain by being configured to operate in a multiple input, multiple output (MIMO) mode, whereby both the camera head 10 and control unit 20 are provided with multiple transmitting antennas 16 and receiving antennas 22, respectively.

By utilizing multiple transmitting antennas 16 and/or receiving antennas 22 that are located at a distance and/or angle relative to one another, the system 5 is able to provide wireless coverage over a larger area than would otherwise be possible. System reliability is also improved through the use of multiple transmitting antennas 16 and/or receiving antennas 22. Specifically, by utilizing two or more transmitting and/or receiving antennas, the system is able to convey multiple wireless signals between the camera head 10 and control unit 20. As a result, potentially detrimental multipath wave propagation effects are reduced, while system redundancy is improved in instances where one wireless signal path becomes blocked or an antenna looses signal.

According to a further embodiment of the invention, the wireless coverage of the system 5 can be maximized by having multiple transmitting and receiving antennas configured to operate in a differential mode. Alternatively, the wireless camera system 5 can have an array of transmitting and/or receiving antennas configured to operate in a switching mode, whereby the system automatically switches signal transmission to the antenna with the strongest signal strength.

As previously discussed, one or more receiving antennas 22 are associated with the control unit 20 so that the control unit is able to receive the wireless camera signal transmitted by the camera head 10. With regard to placement, the receiving antennas 22 can be located essentially anywhere in the surgical room that provides for a high fidelity signal. For example, one embodiment may simply call for multiple receiving antennas 22 to be mounted upon the control unit 20. Other embodiments can incorporate more complex arrangements wherein one or more receiving antennas 22 are located remotely from the control unit 20, for example, mounted upon the walls and/or ceiling, or upon various items or fixtures within the room.

Numerous antenna configurations are also possible with respect to the transmitting antenna(s) associated with the camera head. According to an embodiment illustrated in FIG. 2A, one or more transmitting antennas 210 extend substantially axially outwardly from the distal end of the body of the camera head 200 in a cantilevered manner so as to provide maximum exposure and performance. The directional placement of the antennas 210 can also be adjusted in order to improve performance. For instance, directing the antennas 210 so as to angle downwardly towards the endoscope 202 typically provides the antennas with the greatest exposure, and consequently, results in better performance.

Figure 2B:
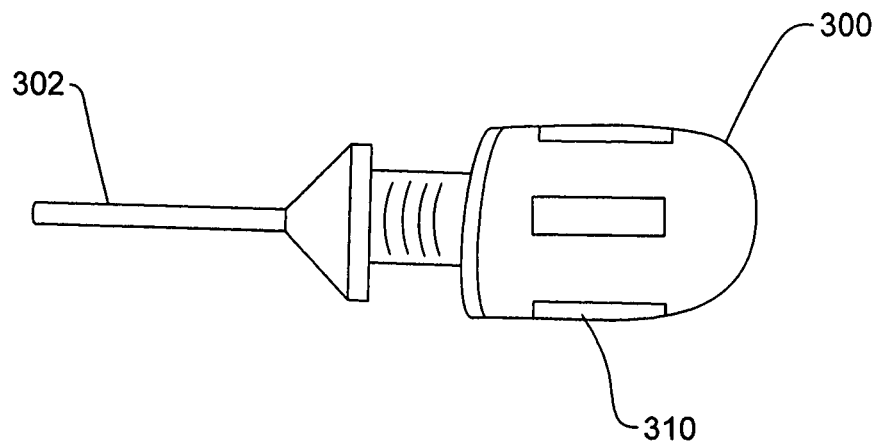
FIGS. 2A-2D illustrate different antenna configurations in plan view (FIGS. 2A and 2B), perspective view (FIG. 2), and longitudinal cross-sectional view (FIG. 2D), for a wireless camera head according to several alternative embodiments of the invention.
Figure 2A:
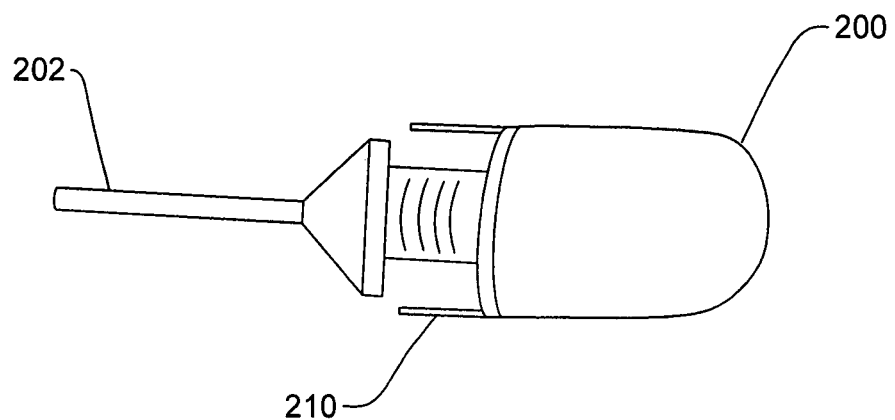

According to an alternative embodiment, one or more transmitting antennas can be mounted upon or integrated into the surface of the camera head. For illustrative purposes, see FIG. 2B, which depicts a wireless camera head 300 attached to an endoscope 302. Multiple transmitting antennas 310 are mounted upon the surface of the camera head 300 in circumferentially spaced relation with one another and in such a manner that the antennas 310 do not extend out from, or are essentially flush with, the body of the camera head 300. A mounting arrangement such as that shown in FIG. 2B provides greater protection to the antennas 310, thereby extending their product life.

Figure 2C:
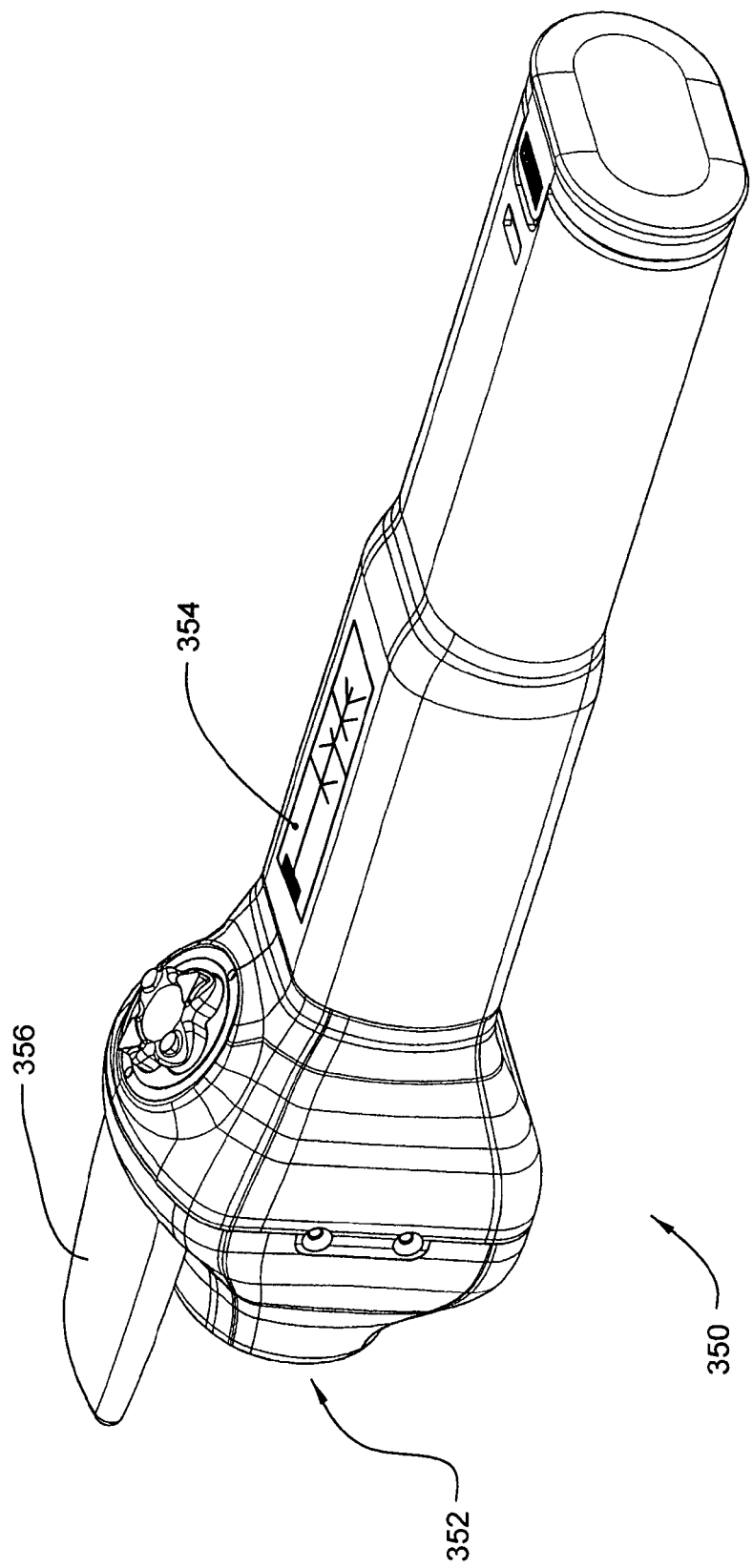
Figure 2D:
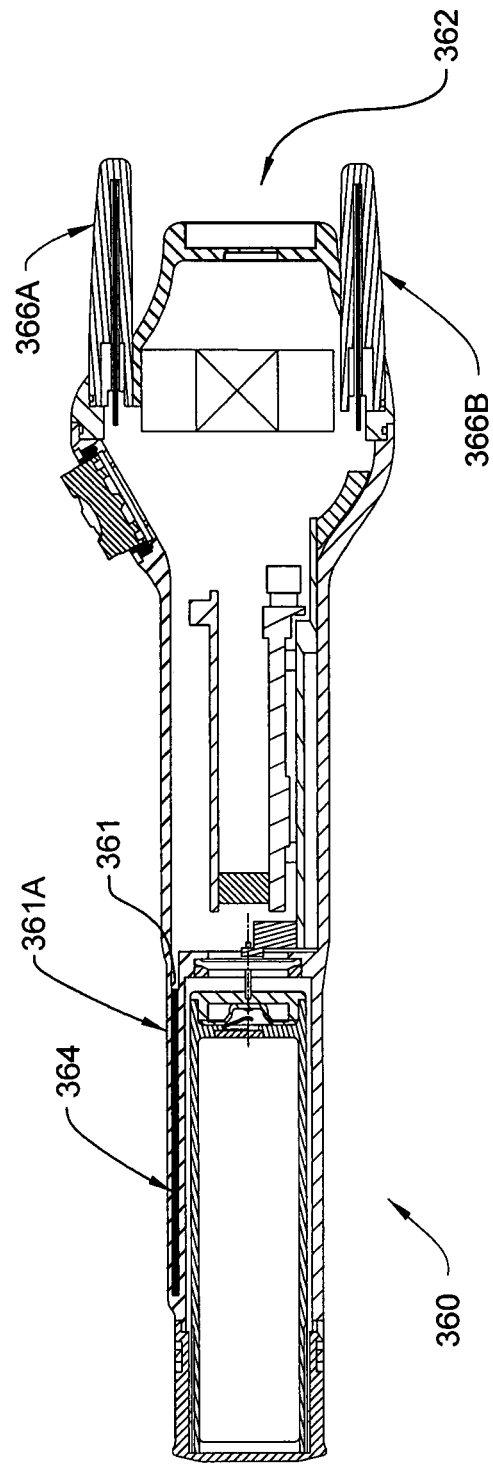

Additional transmitting antenna arrangements are illustrated in the embodiments represented by FIGS. 2C and 2D. Specifically, FIG. 2C is a perspective view of a wireless camera head 350 having a distal end 352 capable of receiving and attaching to an endoscope (not illustrated). To wirelessly transmit the images obtained by the endoscope, camera head 350 incorporates first and second transmitting antennas. The first antenna 354 mounts upon the camera head 350 so as to be essentially flush with the body of the camera head 350. A second transmitting antenna 356 extends out from the camera head 350 in a cantilevered fashion so as to project towards the endoscope and extend in a generally parallel manner with respect to the axis of the endoscope when same is attached to the camera head 350.

FIG. 2D is a cross-sectional view of a wireless camera head 360 according to an alternative embodiment. In this embodiment, camera head 360 is configured to receive an endoscope (not illustrated) at a distal end 362 thereof. A first antenna 364 is incorporated into the camera head 360 so as to be essentially flush with the body of the camera head 360. More specifically, antenna 364 is provided in an elongate recess or slot 361 defined in a housing 361A of camera head 360. Second and third transmitting antennas 366A and 366B, respectively, extend out from opposite sides of the distal end 362 of the camera head 360 in a cantilevered manner and project towards the endoscope when attached to the camera head 360.

In a further embodiment of the invention (not illustrated), a wireless camera head incorporates multiple transmitting antennas that operate in phase or with the same polarization. Alternatively, the camera head can be configured so that one or more of the multiple transmitting antennas operate out-of-phase with respect to the other antennas, thereby producing electromagnetic signals having different polarization.

According to an additional embodiment (not illustrated), a wireless camera head incorporates at least one omnidirectional-type antenna, i.e., a circular antenna, that is capable of effectively transmitting a wireless signal in all directions. One or more directional-type antennas can also be incorporated into the camera head, if desired, to supplement the omnidirectional antenna and improve the performance of the wireless transmission.

Figure 3:
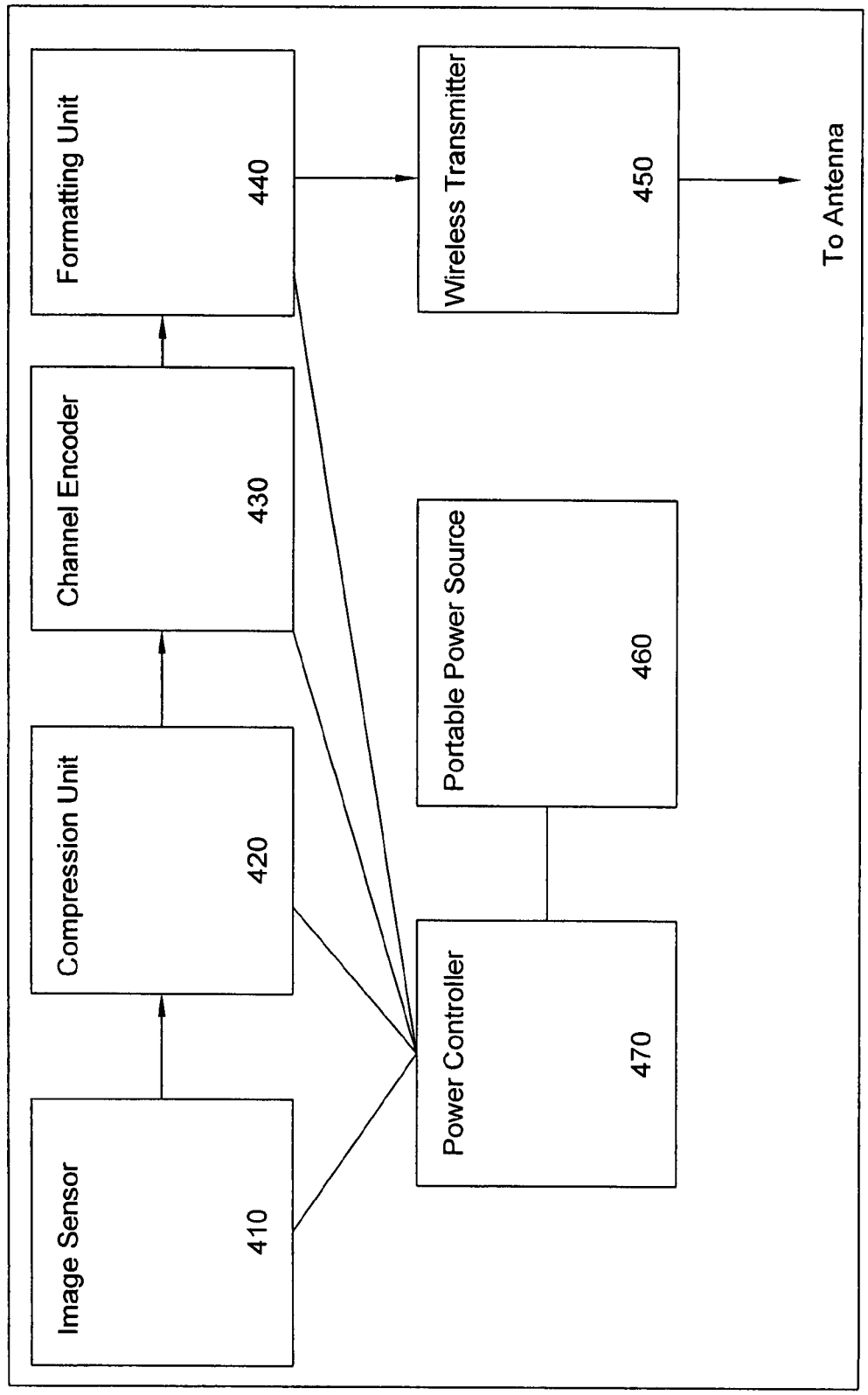
FIG. 3 is a block diagram illustrating the basic components comprising the camera head, as well as the flow of video image data through these components.

The components that comprise camera head 10 will now be discussed in detail with respect to the block diagram of FIG. 3. However, before proceeding, it should be noted that the illustrated embodiment of FIG. 3 depicts the camera head 10 as including an image sensor 410. In this instance, when attached to the camera head 10, an endoscope captures the light making up the image and conveys that light to the image sensor 410, which converts the optical light into a digital signal that can subsequently be transmitted wirelessly to the associated control unit.

However, according to another embodiment (not illustrated), the camera head may not include an image sensor, but instead is configured to receive an image already converted into a digital signal. Specifically, in this embodiment, the endoscope that attaches to the camera head includes its own image sensor that receives the light that makes up the image and converts it to a representative digital signal. Thus, the endoscope captures the image, converts it to a digital signal, and then conveys this digital signal to the camera head. Upon receipt, the camera head further processes the digital image signal and wirelessly transmits the signal to the control unit. Accordingly, in this embodiment, the endoscope represents a stand-alone camera device that is separate from, but capable of connecting to the camera head in order to transfer the digital image signal.

The following discussion relating to FIG. 3 presumes that the camera head 10 includes an image sensor 410. However, it should be understood that the following technical discussion concerning the components of the camera head 10 remains equally applicable to those embodiments where the image sensor is maintained within the endoscope instead of the camera head as discussed above.

Included within camera head 10 is image sensor 410 for converting a pattern of light making up an image into an electrical signal. According to one embodiment, image sensor 410 is configured to have a high sensitivity in order for the camera system to perform well under low light conditions. The image sensor 410 can also be configured to have a high dynamic range so as to be capable of capturing the various gradations of an image from the lightest highlight to the darkest shadow.

The video image signal generated by image sensor 410 is then compressed by compression unit 420, allowing for a greater amount of data to be provided to the control unit over a specified period of time. According to one embodiment, the compression unit 420 processes the image signal utilizing a variable compression algorithm that can vary the rate at which the video image signal is compressed. Furthermore, this compression rate is dynamically adjusted by a rate determination algorithm in response to the quality of the wireless link that currently exists between the camera head 10 and control unit 20, as well as the scene being captured at that moment in time.

The compression unit 420 can be further configured to compress the video image data using either a "lossy" or "lossless" compression scheme. If the compression unit 420 is configured to use a "lossy" compression scheme, selected portions of the video image data is disregarded or thrown out as part of the compression process. This generally allows for data to undergo greater compression at the cost of image quality. In contrast, greatest picture quality will be obtained if the compression unit 420 is configured to use a "lossless" compression scheme, where all of the image data is utilized to generate the video image.

According to one embodiment, the compression unit 420 can be further configured to use a compression algorithm that acts upon individual frames of image data and treats each frame as being independent from other frames. This frame-specific compression algorithm does not benefit from any compression that could otherwise be obtained by more traditional algorithms that typically exploit differences between frames and thus can obtain greater compression when there is a lack of motion in the image. However, the frame-specific compression algorithm utilized in the present embodiment offers the fundamental benefit of lower through-put delay and less error susceptibility.

Specifically, the frame-specific compression algorithm of the present embodiment analyzes and compresses only one image frame of the video signal at a time. In contrast, a typical video compression algorithm such as MPEG2 compresses the signal by analyzing and determining the differences between adjacent image frames of the video signal.

As a consequence of utilizing a frame-specific compression algorithm, the system of the present invention is able to provide low latency between the encoding and decoding of the video/image signal. In particular, the frame-specific image compression algorithm of the present invention is able to encode and decode images with a maximum latency or delay equivalent to one image frame plus associated computational and transmission delays. In contrast, algorithms that are designed to exploit the differences between adjacent image frames, such as traditional video algorithms, are subject to a much greater latency or delay that is equivalent to more than two image frames plus associated computational and transmission delays.

The use of a frame-specific compression algorithm in the current embodiment also provides the wireless endoscopic camera system of the present invention with an enhanced ability to be more error resilient. When an error in an image occurs, any distortion created during image compression and related to that error will be restricted to that particular image frame. In contrast, more traditional compression algorithms that exploit differences between one image frame and an adjacent image frame, an error in the image of one frame will result in distortion in multiple frames.

According to another embodiment, compression unit 420 employs an algorithm that is capable of varying the quality of an image from an encoded bitstream. Upon the wireless transmitting of image data by the camera head, a minimum or base quality image stream is first transmitted with high accuracy using a Forward Error Correcting/Automatic Repeat Request (FEC/ARQ) based approach. Once this initial image stream is transmitted, the camera head proceeds to transmit additional image data that can be utilized by the control unit to generate a higher quality image. This additional image data is progressively transmitted for a fixed duration of time. If there is insufficient time for the system to transmit the higher quality image data following the initial minimum or base quality image stream, then the system drops the rest of the current image and proceeds to initiate transmission of the next image.

In an exemplary embodiment, compression unit 420 is configured to compress the video signal using the JPEG (Joint Photographic Experts Group) 2000 standard. The JPEG 2000 standard produces a frame-accurate signal where every image frame in the original video signal is contained in the compressed video signal. In addition, the JPEG 2000 compression scheme progressively codes the bit stream in such a way that certain data is initially disregarded, resulting in less-detailed information being placed at the beginning of a data stream. As the stream progresses, the system stops disregarding data, resulting in the transmission of more-detailed information later on in the data stream. As a result, the video signal can generate images at different resolutions or quality levels. For example, lower-resolution images may be directed to a video monitor, while higher-resolution images from the same video signal are directed to a video recorder for archiving.

Similar to the previously discussed compression algorithm, the JPEG 2000 standard is a frame-specific compression scheme that provides for low latency encoding and decoding, as well as increased resiliency to errors. In addition, the JPEG 2000 standard further incorporates resynchronization markers and the coding of data into relatively small independent blocks, as well as mechanisms to detect and conceal errors within each block, making JPEG 2000 more error resilient compared to several traditional compression schemes such as JPEG and MPEG2.

JPEG 2000 also provides the ability to transmit a "lossless" image on demand. According to this embodiment, the wireless endoscopic camera system can be configured to transmit a "lossy" digital image during an endoscopic surgical procedure. However, during certain occasions, the surgeon may require a higher-quality image for diagnostic purposes. The JPEG 2000 encoder has the ability to generate a "lossless" image on demand using the same encoding mechanism used for the typical "lossy" image. In response to the surgeon's request for a higher quality image, the camera head encodes the image in a lossless fashion and wirelessly transmits the complete image utilizing a FED/ARQ mechanism. The additional processing required to produce the "lossless" image does lead to increased delays in image transmission. However, in such circumstances, any increased transmission delays are typically not noticed as surgeons usually expect a short delay to occur while capturing a "freeze frame" image of the video signal.

A further advantage provided by the JPEG 2000 image compression standard is an ability to perform selected encoding based on a region of interest (ROI) of the image. More specifically, during a surgical situation, there may be regions of a video scene that are perceived to be more important than other regions, i.e., part of the video image is outside the field of view of the endoscope, and thus contains no useful information. In this circumstance, the useless region of the video scene can be encoded at a very low rate, thereby conserving processing power, memory and bandwidth, while the pertinent regions of the video scene are encoded at a high rate that provides for a good quality image.

According to another embodiment, the wireless endoscopic camera system transmits the critical parts of a video stream, e.g., the header data, on a sub-channel that is more reliable while the rest of the data is transmitted normally. This sub-channel is created as a time-dependent, error-corrected channel for critical information.

Once compressed, the video image data is processed by channel encoder 430 so as to implement a RF link-dependent Forward Error Correcting (FEC) code as part of the video signal, whereby redundancy is added to the transmitted image data through the use of a predetermined algorithm. This allows the system to detect and correct errors in the transmitted signal, and thus improve the fidelity of the wireless channel.

Another embodiment includes a limited Automatic Repeat Request (ARQ) that is implemented either alongside the FEC code or by itself in order to provide higher fidelity on the wireless channel. ARQ is an error control method for data transmission, whereby if the receiver detects transmission errors in a message, it will automatically request a retransmission from the transmitter.

Once encoded, the video image data passes on to the formatting unit 440 where the data undergoes final preparation before being wirelessly transmitted. The actual type of preparation that the data undergoes will vary depending on the wireless technology/standard utilized by the endoscopic camera system. For instance, various manipulations such as Fast Fourier Transformation algorithms may be applied. The video image data making up the video signal may also be separated into different streams that will be transmitted at different channels or frequencies.

According to one exemplary embodiment, the endoscopic camera system utilizes Ultrawideband (UWB) technology to wirelessly transmit the video signal from the camera head to the control unit. UWB is a wireless radio technology designed for transmitting data over short distances (up to 20 meters) at very high data rates (500+Mbps). To accomplish high data rates, UWB transmits over a wide range of radio spectrum, using a series of very narrow and low-power pulses. As of the year 2005, the Federal Communications Commission defined UWB wireless transmissions as being a transmission from an antenna for which the emitted signal bandwidth exceeds the lesser of 500 MHz or 20% bandwidth, and authorized the unlicensed use of UWB within the 3.1 to 10.6 GHz spectrum.

One specific UWB-based standard that could be effectively utilized in the current embodiment is known as MultiBand Orthogonal Frequency Division Multiplexing (MB-OFDM). As a result of transmitting data simultaneously over multiple carriers spaced apart at precise frequencies, the MB-OFDM standard produces wireless transmissions that are resilient to RF interference and multipath effects.

Formatting unit 440 also monitors signal transmission and wireless link status by means of one or more algorithms. For example, a media access algorithm (MAC) is responsible for determining the availability of a wireless channel/frequency. Once the MAC algorithm determines an available channel, the now compressed and encoded video image data is wirelessly transmitted to the control unit by wireless transmitter 450.

Beyond the image sensor and signal processing components 410-440, the camera head 10 also incorporates a power source 460 and power controller 470. Power source 460 can be any type of portable energy source, such as, for example, a nickel metal-hydride or lithium ion rechargeable battery, or a disposable alkaline battery.

In an alternative embodiment, camera head 10 is configured to simultaneously accept two or more batteries. This dual battery system is configured to allow one battery to be replaced while the other battery continues to power the camera head 10.

According to a further embodiment, one of the batteries in the dual battery system is replaced with a capacitor that is sufficiently large enough to be capable of temporarily powering the camera head 10 while the battery is being replaced. During such an occurrence, the video signal being generated by the endoscopic camera may be temporarily lost. However, by means of the capacitor, the camera head 10 would continue to receive the minimum amount of power necessary to maintain the context or current operating state of the system. Upon replacement of the battery and restoration of full-power, the video signal returns and the camera head 10 continues to operate just as it was prior to the battery replacement.

In an additional embodiment, the camera head 10 incorporates a non-volatile memory for storing camera head settings or operating context. Upon loss of power, such as during replacement of the battery, the settings and configurations that define the current operating state of the camera head 10 are written to the non-volatile memory. Upon restoration of power to the camera head 10, the last operating state settings of the camera head 10 are retrieved and re-established.

Figure 4:
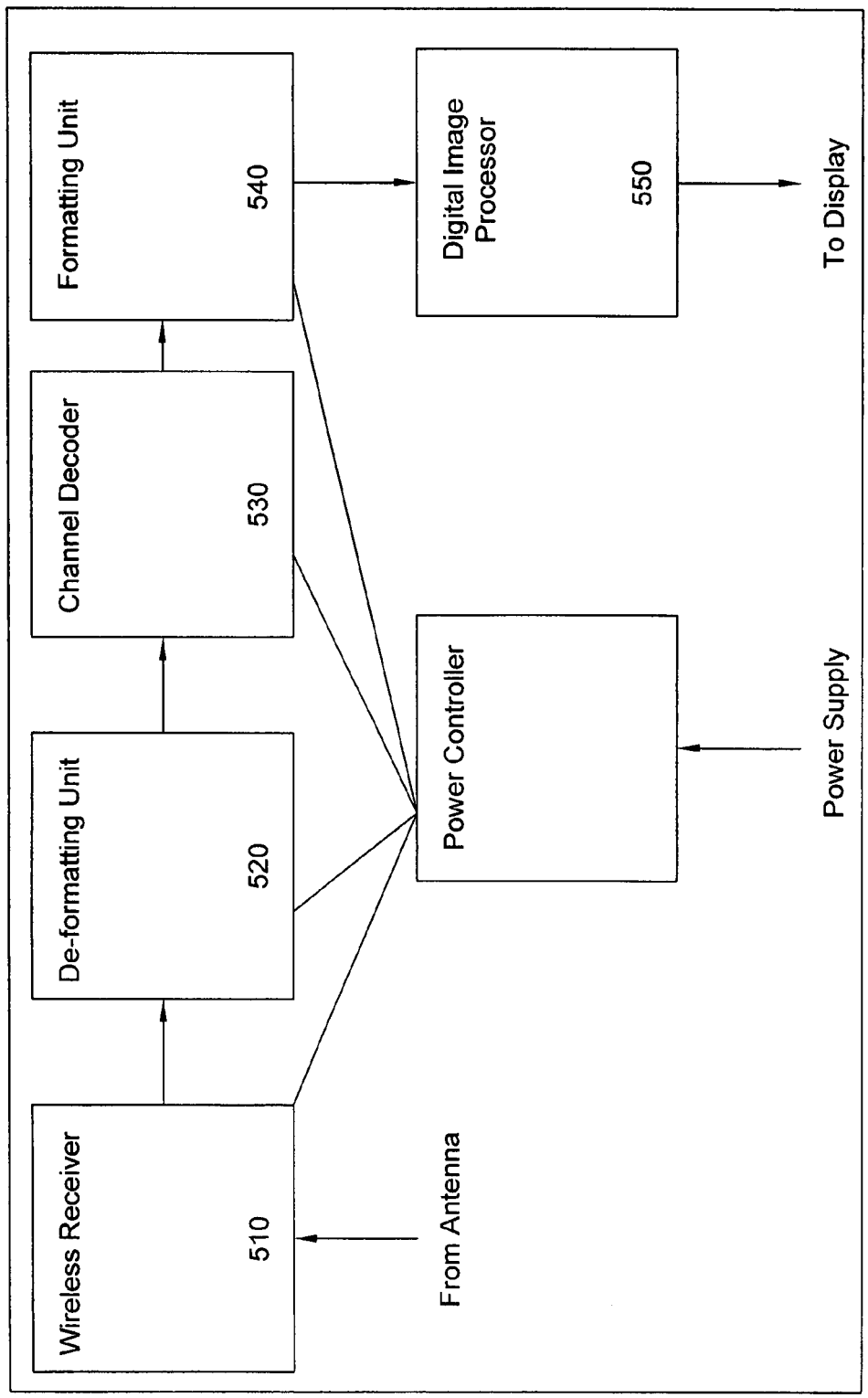
FIG. 4 is a block diagram illustrating the basic components comprising the control unit, as well as the flow of video image data through these components.

The wireless signals transmitted by the camera head 10 are subsequently picked up and processed by the control unit 20. Specifically, the wireless signals are acquired by one or more receiving antennas and conveyed to the control unit 20. The video signal subsequently undergoes processing by the control unit 20 in a reverse manner so as to get the signal back to its original state. As illustrated in FIG. 4, numerous components are required in order to process the wireless signal in reverse so as to generate the original or intended digital image.

After being received by the antenna, a wireless video signal is conveyed to the wireless receiver 510 and subsequently on to a de-formatting unit 520, which removes from the video signal any previous formatting originally required to transmit the signal wirelessly.

The video image data making up the received signal is then conveyed to a channel decoder 530, which reverses the encoding previously carried out by the camera head, as well as removes the previously implemented Forward Error Correcting (FEC) code.

Once the video image data making up the signal has been decoded, it has to be decompressed by decompression unit 540. If the video image data was originally compressed by a lossless compression scheme, then the decompression unit 540 can reverse the compression process to generate the exact video signal as originally generated by the image sensor. If the video image data was originally compressed by a lossy compression scheme, resulting in portions of the data signal being discarded, then the decompression unit 540 attempts to reverse the compression process and generate a video signal that is a close approximation of the original video signal.

The decompressed video signal should now be equivalent to, or approximately equivalent to, the original video signal generated by the image sensor of the camera head. The video signal can then be conveyed to one or more peripheral devices, including a video monitor 30 where the signal is converted back to an image that can be viewed on the monitor 30. Additional peripheral devices can include, for example, a video recorder or printer.

According to another embodiment and referring back to FIG. 1, a cable 18A can connect to both the camera head 10 and control unit 20 so as to establish a wire connection between them. Specifically, both camera head 10 and control unit 20 can be provided with cable interfaces 18 and 24, respectively. The cable 18A connects between the two cable interfaces 18 and 24, and is capable of being sterilized. During an emergency situation, for example, a lack of charged batteries or the presence of significant RF interference preventing wireless communication, the sterilized cable 18A could be plugged into interfaces 18 and 24 so as to provide a wire connection between the camera head 10 and control unit 20. In addition to carrying video signals from the camera head 10 to the control unit 20, the system can also be configured so that the control unit 20 can power the camera head 10 by means of the cable 18A.

In an alternative embodiment (not illustrated), cable 18A does not connect to camera head 10 by means of interface 18. Instead, one end of cable 18A terminates with a plug that approximates the size and shape of the battery accepted by the camera head 10. When a cable connection to the camera head 10 is desired, the battery is simply removed from the camera head 10 and replaced with the battery-resembling plug of cable 18A.

Many modern-day endoscopic surgeries require the use of multiple cameras to either generate views of different anatomical features, or different views of the same anatomical feature. Multiple camera systems are also being utilized more frequently in specialized surgical settings, such as, for example, surgeries requiring the generation of a stereoscopic or 3-D view of a surgical scene. As such, it is envisioned that the wireless endoscopic camera system of the present invention will be used in surgical settings that require multiple cameras. According to one embodiment, first and second endoscopes and associated wireless camera heads transmit first and second wireless video signals that are received and processed by first and second control units, respectively. Alternatively, the first and second camera heads, and corresponding wireless signals, are received and processed by a single control unit.

In either situation presented above, it is desirable to minimize the possibility of wireless interference or misdirected communications that may occur between two or more wireless endoscopic camera systems, or two or more wireless endoscopic camera heads being utilized within a single system. To address the above concern, a further embodiment of the wireless endoscopic system incorporates means for locking the transmitter of a specific camera head 10 to the receiver of a specific control unit 20. Once locked, the receiver will only acknowledge wireless signals originating from its corresponding transmitter.

The locking of a transmitter to a receiver can be accomplished in numerous ways, including the utilizing of a second wireless communication channel between the transceiver of the camera head and the receiver of the control unit. Alternatively, the system can be configured so that the transceiver of a camera head must initially synchronize to a receiver so that the receiver will only acknowledge wireless signals that contain an identification code unique to the corresponding transmitter. To initiate the above locking process, a transceiver and receiver must be synchronized. This synchronizing process can be carried out in numerous ways, ranging from being programmed manually, to being configured automatically based on data retrieved through the wireless scanning of a barcode or reading of a RFID tag located on the control unit and/or camera head.

In another embodiment, the wireless endoscopic camera system includes an endoscope that incorporates an image sensor capable of generating a digital image signal. Once generated, the digital image signal is transferred to the attached camera head by means of a direct electrical contact such as a wired connection. However, according to an alternative embodiment, the digital image signal is wirelessly transferred from the endoscope to the camera head.

Figure 5:
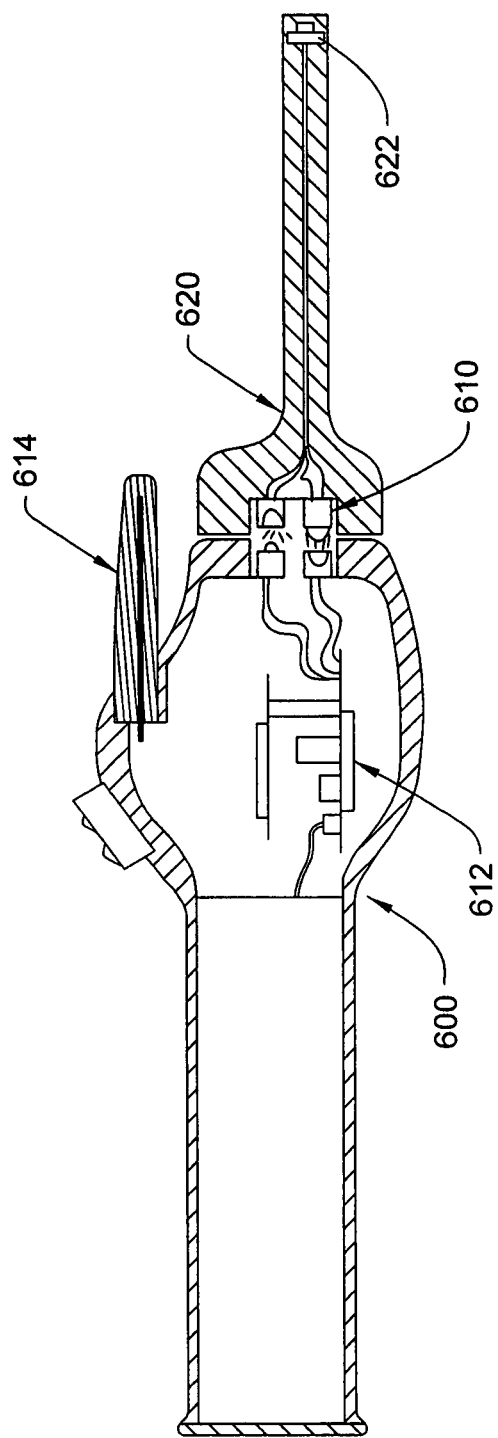
FIG. 5 illustrates a wireless endoscopic camera system in a longitudinal cross-sectional view incorporating a wireless, optical-based communications link between the camera and camera head.

Specifically, in an alternative embodiment illustrated in FIG. 5, a wireless data connection between camera head 600 and endoscope 620 is achieved by means of a non-contact optical link 610, such as, for example, an infra-red or laser-based communication circuit that is completed when endoscope 620 is attached to camera head 600. The surgical image is captured by an image sensor 622 of the endoscope 620, converted to a digital image signal, and then conveyed to the optical link 610, which wirelessly transmits the digital signal to the camera head 600 as a sequence of light pulses. Once transmitted by the optical link 610, the digital image signal is processed by control circuitry 612 of the camera head 600 and then conveyed to antenna 614, which wirelessly transmits the processed digital image signal to the control unit or other appropriate receiver.

Figure 6:
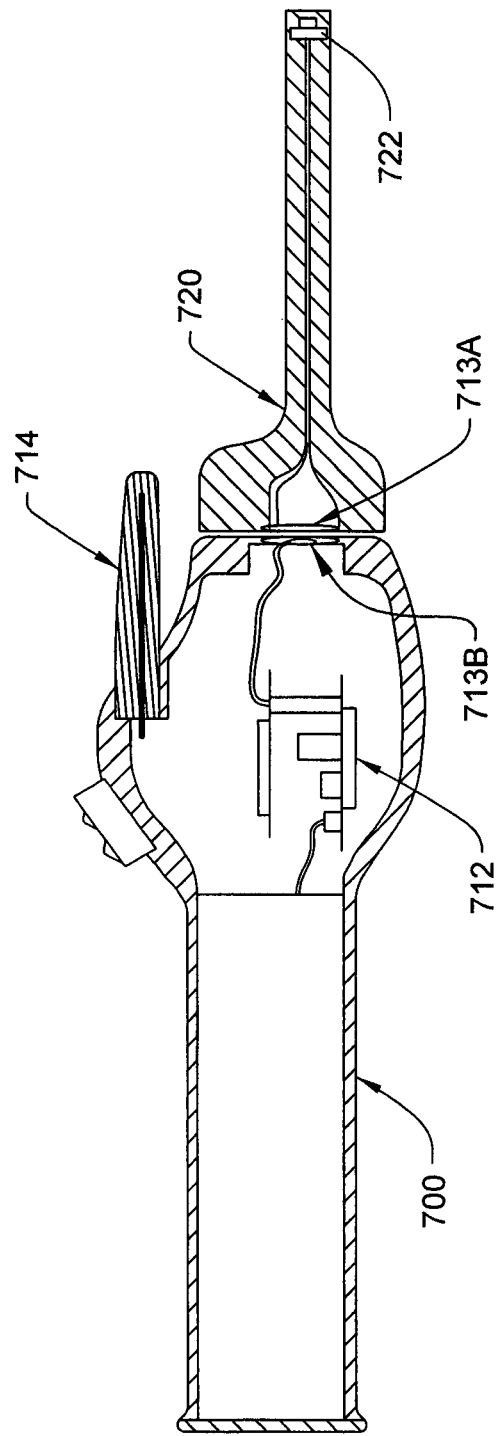
FIG. 6 illustrates a wireless endoscopic camera system in a longitudinal cross-sectional view incorporating a non-contact RF communication link between the camera and camera head.

According to a further alternative embodiment illustrated in FIG. 6, a wireless data connection between camera head 700 and endoscope 720 is achieved by means of a non-contact radio frequency (RF) link. Specifically, endoscope 720 incorporates a first image antenna 713A, while camera head 700 incorporates a similar image antenna 713B. Attachment of the endoscope 720 to the camera head 700 places the image antennas 713A and 713B in close proximity to one another. Endoscope 720 generates and conveys a digital image signal to image antenna 713A, which then proceeds to wirelessly transmit the digital image signal to image antenna 713B of camera head 700. Upon receipt of the digital image signal, camera head 700 processes and wirelessly transmits the digital signal as discussed in the previous embodiment.

Figure 7:
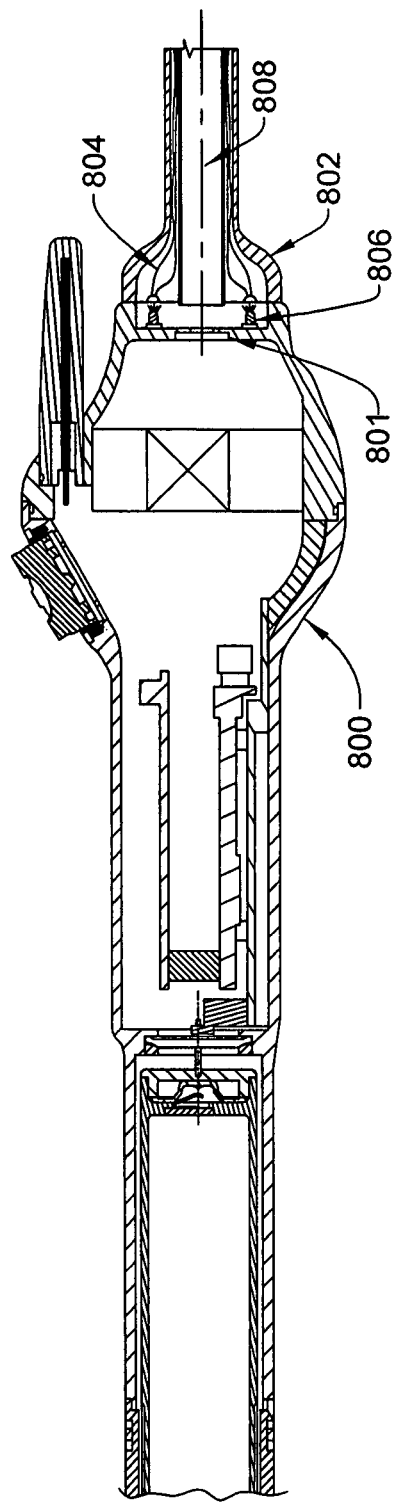
FIG. 7 is a longitudinal cross-sectional fragmentary view of a wireless camera head incorporating a LED array according to one embodiment.

Another embodiment of the present invention includes a wireless endoscopic camera system that generally includes a camera head that connects to an endoscope and which can wirelessly transmit digital images, obtained by the endoscope, from the camera head to a control unit. As illustrated in FIG. 7, a wireless endoscopic camera head 800 is configured to receive an endoscope 802 at the distal end of the camera head 800. Also mounted on the distal end of the camera head 800 is an array of light emitting diodes (LED's) 806 arranged in a generally circular pattern that facilitates the direct coupling of an endoscope 802 to the camera head 800, as well as facilitates the rotation of an attached endoscope 802 relative to the camera head 800.

When endoscope 802 is attached to camera head 800, the array of LED's 806 is aligned with the proximal ends of a plurality of fiberoptics 804 that are also arranged in a generally circular pattern but which extend along the length of the endoscope 802. In this manner, when endoscope 802 is attached to camera head 800, the array of LED's 806 becomes optically coupled to the fiberoptics 804, with the light emitted from the LED's 806 entering the fiberoptics 804 and traveling down the length of the endoscope 802 to ultimately be projected out from the distal end of the endoscope 802 so as to illuminate the surgical scene being observed by the endoscope 802. A portion of the light projected upon the surgical scene becomes reflected and returns back towards the distal end of the endoscope 802. A portion of this reflected light enters an optical tube assembly 808 that extends centrally through the endoscope 802 and is conveyed back to the proximal end of the endoscope 802, where the light is then conveyed on to an image sensor 801 that is either incorporated into the endoscope 802, or alternatively, incorporated into the camera head 800.

Figure 8:
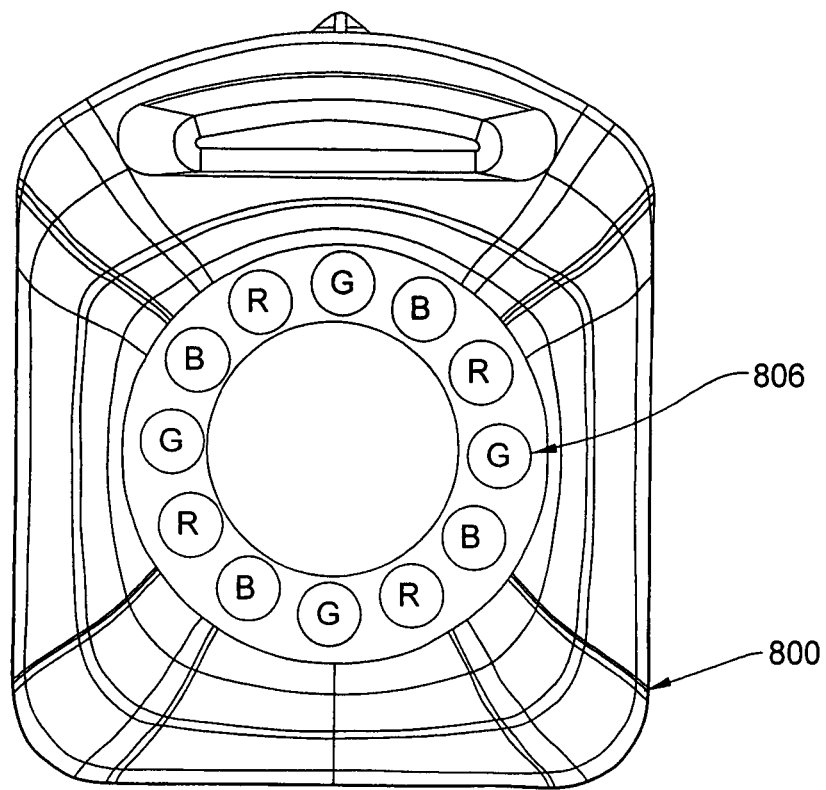
FIG. 8 is an end view of the camera head of FIG. 7, with the endoscope detached therefrom so as to illustrate the LED array.

As further illustrated in FIG. 8, which depicts a distal end view of the camera head 800 of FIG. 7, the array of LED's 806 comprises a plurality of red, green and blue LED's. Control of these LED's 806 is carried out by an electronic control circuit (not illustrated) that is maintained within the camera head 800. By means of this control circuit, each LED 806 can be independently controlled relative to the other LED's within the array. By then adjusting the levels at which the red, green and blue LED's are driven, a user can adjust the color temperature of the light being projected upon the surgical scene, and thus obtain an optimal light spectrum for each specific surgical case.

According to another embodiment (not illustrated), a camera head similar to that depicted in FIG. 7 also contains an array of LED's arranged at a distal end of the camera head, such that when the camera head is attached to an endoscope, the light generated by the LED's is conveyed into a plurality of fiber optics that extend along the length of the endoscope. However, unlike the previous embodiment, the plurality of LED's in the current embodiment all generally emit light of the same frequency spectrum (e.g., white light LED's).

Figure 9:
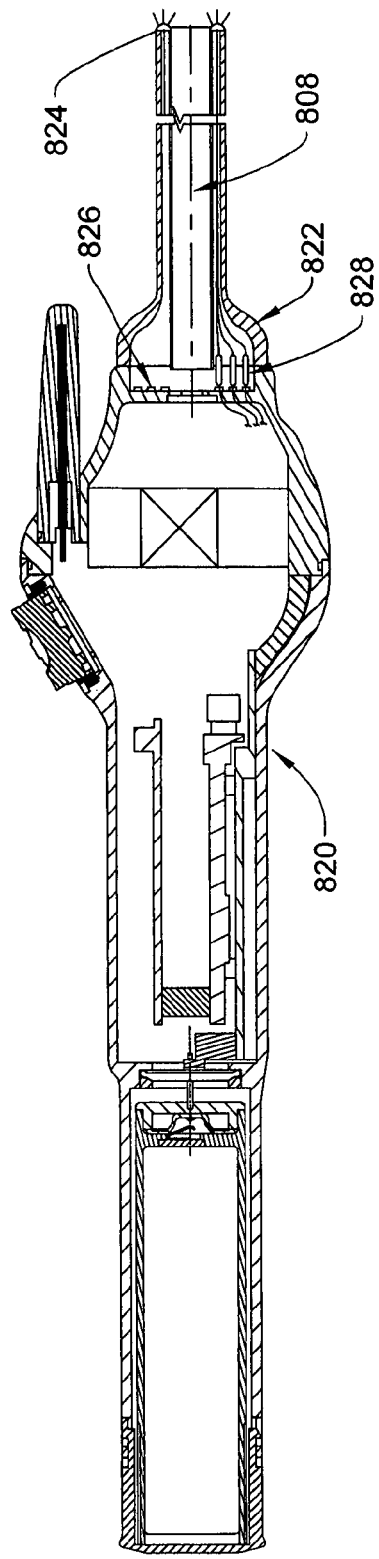
FIG. 9 is a longitudinal cross-sectional view of a wireless camera head according to one embodiment that incorporates an electrical interface between the camera head and attached endoscope.

In a further embodiment as illustrated in FIG. 9, a wireless endoscopic camera head 820 is configured to attachably receive an endoscope 822 at its distal end. Endoscope 822 incorporates one or more power-consuming components or features, such as, for example, an LED array 824 or other light source, or alternatively, an image sensor (not illustrated). To facilitate the use of powered components, an electrical interface between the camera head 820 and endoscope 822 is provided that allows for the transmission of electrical power and/or control signals from the camera head 820 to the endoscope components (i.e., LED array 824).

The electrical interface comprises a series of contact rings 826 mounted upon the camera head 820, and a plurality of electrical contacts 828 that are incorporated into the endoscope 822 in such a manner that the contacts 828 project out from the proximal end of the endoscope 822.

Figure 10:
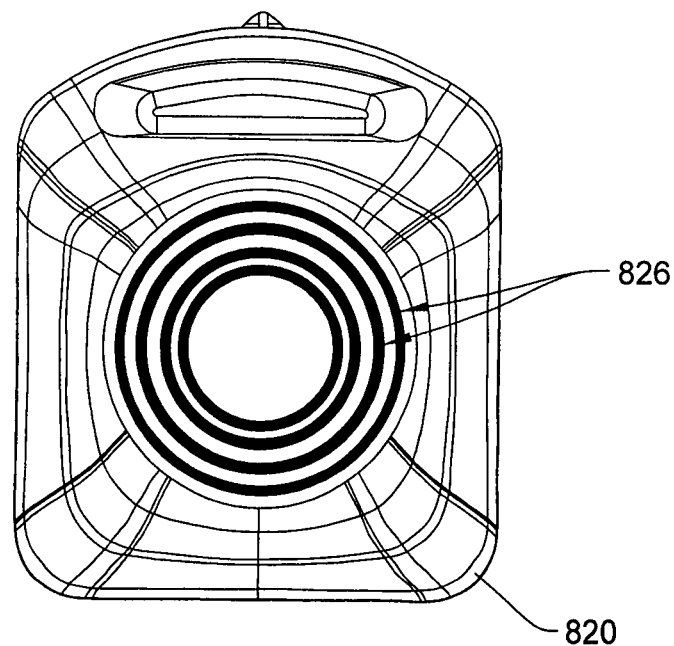
FIG. 10 is an end view of the camera head of FIG. 9 with the endoscope removed therefrom so as to illustrate the electrically energized, concentric contact rings.

As illustrated in FIG. 10, which depicts an end view of the distal end of the wireless camera head 820, the contact rings 826 comprise a series of electrically energized, generally concentrically-oriented contact rings 826 fixed upon the camera head 820. Upon attachment of the endoscope 822 to camera head 820, the electrical contacts 828 that project out from the endoscope 822 align up and come into contact with the electrically energized, concentric contact rings 826. Each electrical contact 828 will be maintained in constant contact with its corresponding concentric contact ring 826 for as long as the endoscope 822 is attached to camera head 820. Furthermore, the annular design of the contact rings 826 assures that the electrical connection between the endoscope 822 and camera head 820 is maintained even when the endoscope 822 and camera head 820 are rotated relative to one another.

Figure 11:
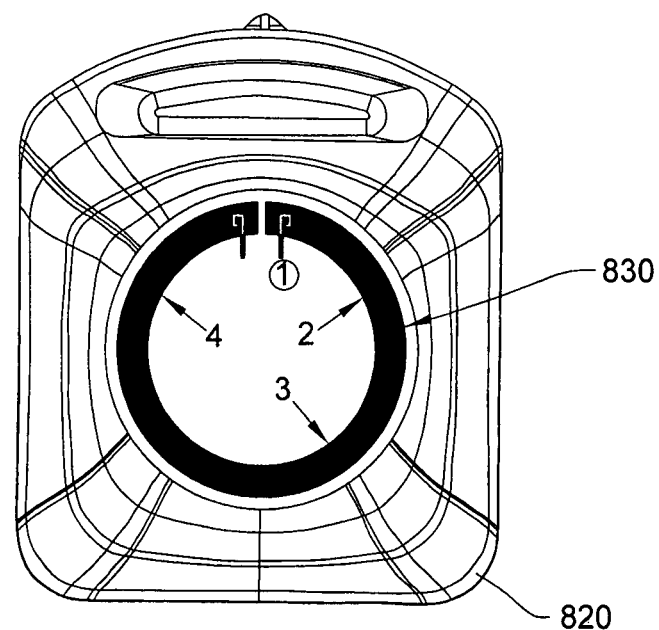
FIG. 11 is an end view of a camera head incorporating an electrically energized, variable resistance contact ring.

The embodiment illustrated in FIGS. 9 and 10 provides for the ability to provide electrical power and control signals to one or more components of an endoscope by means of an electrical interface that exists between the camera head and endoscope, while allowing full rotation of either device relative to the other. However, according to a further embodiment, the electrically-energized, concentric contact rings 826 are replaced by a single electrically-energized, variable resistance ring 830. Similar to the concentric rings 826, the variable resistance ring 830, as illustrated in FIG. 11, provides an electrical connection between the endoscope and wireless camera head while allowing either device to freely rotate relative to the other.

However, unlike the concentric rings 826, the variable resistance ring 830 exhibits an electrical resistance that varies relative to angle, i.e., 1-2, 1-3, 1-4. Consequently, the resistance ring 830 will exhibit differing levels of electrical resistance depending on the angle of rotation present between the endoscope and wireless camera head. As a result, the system can monitor the level of electrical resistance currently being exhibited by the resistance ring 830, and based on that information, determine the angle of rotation that the endoscope has undergone relative to the camera head.

Figure 12:
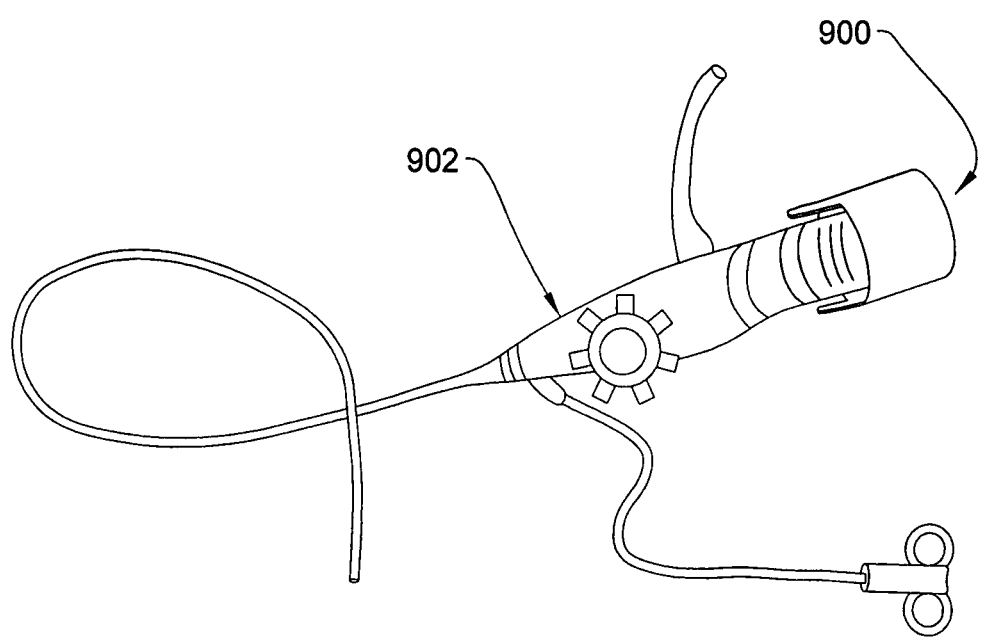
FIG. 12 illustrates a wireless endoscopic camera system comprising a wireless camera head attached to a flexible endoscope.

In the illustrated embodiments described above, the wireless camera head has been depicted as being utilized with a rigid-type of endoscope, such as those that might be used in laparoscopic and thoracoscopic surgical procedures. However, the present invention is not limited to use with rigid-types of endoscopes, but instead can be utilized with essentially any type of endoscope as long as the endoscope and/or camera head have been appropriately configured to attach to and communicate with one another. To illustrate the above, consider the embodiment of FIG. 12, which depicts a wireless camera head 900 detachably connected to a flexible endoscope 902 such as an esophagoscope or colonoscope.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A wireless endoscopic camera system, comprising:
   a surgical endoscope for viewing tissue within the body of a patient;
   a camera head for processing digital image data representative of an endoscopic image viewed by the endoscope, the camera head having a proximal end and a distal end, with the distal end detachably connected to the endoscope;
   a compression unit contained within the camera head for reducing the amount of digital image data required to represent the endoscopic image;
   a transmitter contained within the camera head for conveying the compressed digital image data to a remote receiver; and
   a plurality of antennas located on a body of the camera head and in communication with the transmitter for receiving the compressed digital image data from the transmitter and wirelessly relaying the compressed digital image data to the remote receiver, wherein at least one of the plurality of camera head antennas is disposed near the distal end of the camera head and projects outwardly beyond the distal end of the body of the camera head.

2. The wireless endoscopic camera system according to claim 1:
   wherein the remote receiver includes a plurality of antennas for receiving the compressed digital image data wirelessly conveyed by the transmitter; and
   wherein the wireless endoscopic camera system operates in a multiple input, multiple output (MIMO) mode, whereby the compressed digital image data is simultaneously conveyed along multiple wireless paths between the transmitter and the remote receiver.

3. The wireless endoscopic camera system according to claim 1, wherein at least a second one of the plurality of camera head antennas is mounted upon the camera head so as to be essentially flush with the body of the camera head, wherein the camera head is configured for grasping by a surgeon during a procedure.

4. The wireless endoscopic camera system according to claim 1, wherein the plurality of camera head antennas are cantilevered outwardly from the body of the camera head so as to be generally parallel with a longitudinal axis of an endoscope detachably connected to the distal end of the camera head.

5. The wireless endoscopic camera system according to claim 1, wherein at least one of the plurality of antennas is an omnidirectional antenna.

6. The wireless endoscopic camera system according to claim 1, wherein the remote receiver includes a plurality of antennas, and wherein the plurality of antennas located on the body of the camera head and the plurality of antennas of the remote receiver operate in a differential mode.

7. The wireless endoscopic camera system according to claim 1, wherein the plurality of antennas located on the body of the camera head operate in a switching mode whereby transmission of the digital image data is automatically routed to the antenna having the strongest signal strength.

8. The wireless endoscopic camera system according to claim 1, wherein the transmitter configures the plurality of antennas to operate in phase.

9. The wireless endoscopic camera system according to claim 1, wherein the transmitter configures the plurality of antennas so that at least one antenna operates out-of-phase with respect to the other antennas.

10. The wireless endoscopic camera system according to claim 1, wherein all wireless transmissions by the transmitter fall within a 3.1 GHz to 10.6 GHz radio spectrum.

11. The wireless endoscopic camera system according to claim 1, comprising:

an image sensor disposed at the distal end of the endoscope; and a wireless communications link providing the digital image data from the endoscope to the camera head for processing.

12. The wireless endoscopic camera system according to claim 11, wherein the compression unit includes a processor that compresses the digital image data one image frame at a time, with the compression of each image frame of data being conducted independently of any other image frame of data.

13. The wireless endoscopic camera system of claim 1, wherein the endoscope has a proximal end and a distal end, with at least one electrical contact disposed at the proximal end, the proximal end of the endoscope being detachably and rotatably connected to the distal end of the camera head, and wherein the camera head includes at least one electrically-energized contact ring for supplying power to the at least one electrical contact disposed at the proximal end of the endoscope, and wherein the power illuminates light emitting diodes disposed on the endoscope.

14. A wireless endoscopic camera system, comprising:

a surgical endoscope for viewing tissue within the body of a patient;

a camera head for processing digital image data representative of an endoscopic image viewed by the endoscope, the camera head having a proximal end and a distal end, with the distal end detachably connected to the endoscope;

a compression unit contained within the camera head for reducing the amount of digital image data required to represent the endoscopic image;

a transmitter contained within the camera head for conveying the compressed digital image data to a remote receiver; and a plurality of antennas located on a body of the camera head and in communication with the transmitter for receiving the compressed digital image data from the transmitter and wirelessly relaying the compressed digital image data to the remote receiver, wherein the plurality of antennas located on the body of the camera head comprises at least one antenna that is mounted upon the camera head so as to be essentially flush with the body of the camera head, and at least a second antenna of the plurality of antennas that is cantilevered from the body of the camera head so as to be generally parallel with a longitudinal axis of an endoscope detachably connected to the distal end of the camera head and to project outwardly beyond the distal end of the camera head.

15. A wireless endoscopic camera system, comprising:

a surgical endoscope for viewing tissue within the body of a patient, the endoscope having a proximal end and a distal end;

a camera head for processing digital image data representative of an endoscopic image viewed by the endoscope, the camera head having a proximal end and a distal end, with the distal end detachably connected to the proximal end of the endoscope;

a compression unit provided with the camera head for reducing the amount of digital image data required to represent the endoscopic image;

a transmitter provided with the camera head for conveying the compressed digital image data to a remote receiver; and at least one antenna located on a body of the camera head and in communication with the transmitter for receiving the compressed digital image data from the transmitter and wirelessly relaying the compressed digital image data to the remote receiver, wherein the at least one antenna is cantilevered outwardly from the body of the camera head so as to be generally parallel with a longitudinal axis of the endoscope, and wherein the at least one antenna extends outwardly beyond the distal end of the camera head and overlays a portion of the proximal end of the endoscope.

16. The wireless endoscopic camera system according to claim 15, wherein one or more of the at least one antenna is mounted upon the camera head in such a manner so as to be essentially flush with the body of the camera head.

17. The wireless endoscopic camera system according to claim 15, wherein the at least one antenna comprises a plurality of antennas on the body of the camera head.

18. The wireless endoscopic camera system according to claim 15, wherein all wireless transmissions by the transmitter fall within a 3.1 GHz to 10.6 GHz radio spectrum.

19. The wireless endoscopic camera system according to claim 15, wherein all wireless transmission from the transmitter have a data rate equal to or exceeding 50 Mbit/sec.

* * * * *